United States Patent [19]

Holtkamp

[11] Patent Number: Plant 5,599

[45] Date of Patent: Dec. 17, 1985

[54] AFRICAN VIOLET PLANT NAMED SOUTH DAKOTA

[75] Inventor: Reinhold Holtkamp, Isselburg, Fed. Rep. of Germany

[73] Assignee: Gessellschaftsvertrag uber die Ergindergemeinschaft "OPTIMARA", Rees Haffen, Fed. Rep. of Germany

[21] Appl. No.: 471,650

[22] Filed: Mar. 3, 1983

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Schwartz, Jeffery, Schwaab, Mack, Blumenthal & Koch

[57] ABSTRACT

A new cultivar of African violet named South Dakota particularly characterized by its vigorous growth habit, profuse bouquet positioned on upright flower stems; deep violet purple flower color, with the centers of the flower being relatively darker; single flower form; dark green leaves, and its long lasting and non-dropping flowers.

1 Drawing Figure

1

The present invention comprises a new and distinct cultivar of African violet plant, botanically known as *Saintpaulia ionantha,* and hereinafter referred to by the cultivar named South Dakota.

The new cultivar was referred to during the breeding and selection process by the designation D 210/3, and is a product of a planned breeding program. South Dakota was originated from a cross made in a controlled breeding program in Isselburg, West Germany, in 1978. The female, or seed parent was a cultivar designated Wisconsin disclosed in my U.S. Plant Pat. No. 4,353. The male, or pollen parent was a cultivar designated B 229/11 pink single.

The new cultivar South Dakota was discovered and selected by me as a flowering plant within the progeny of the stated cross in a controlled environment in Isselburg, West Germany. Asexual reproduction of the new cultivar by leaf cuttings, as performed by me at Isselburg, West Germany, has demonstrated that the combination of characteristics as herein disclosed for the new cultivar are firmly fixed and are retained through successive generations of asexual reproduction.

South Dakota has not been observed under all possible environmental conditions. The phenotype may vary significantly with variations in environment such as temperature, light intensity and day length. The following observations, measurements and values describe the new cultivar as grown in Isselburg, West Germany, under greenhouse conditions which closely approximate those generally used in commercial practice.

The following traits have been repeatedly observed and are determined to be basic characteristics of South Dakota, which in combination distinguish this African violet as a new and distinct cultivar:

1. Vigorous growth habit.
2. Profuse blooming habit, producing a full bouquet of flowers positioned on upright flower stems well above the foliage.
3. Deep violet purple color, with the center of each flower being relatively darker thus providing a unique appearance.
4. Dark green leaves.
5. The flowers are long lasting and non-dropping, drying on the stems. The flower color fades slightly with maturing.

2

The accompanying photographic drawing shows a typical specimen plant of the new cultivar. The colors appearing in the photograph are as true as possible with color illustrations of this type.

In the following description, color references are made to The Royal Horticultural Society Colour Chart (H.C.C.), issued by Wilson Colour Ltd., and to The Royal Horticultural Society Colour Chart (R.H.S.), except where general colors of ordinary significance are referred to. Color values were taken at approximately 1-2:00 P.M. under natural light conditions at Nashville, Tenn.

Botanical classification: *Saintpaulia ionantha,* Ramat. cv South Dakota.

Parentage:

*Male parent.*—B 229/11 Pink single.

*Female parent.*—Wisconsin U.S. Plant Pat. No. 4,353.

Propagation: The new cultivar holds its distinguishing characteristics through successive propagations by leaf cuttings and by division of shoots.

Plant: From 7 cm. to 10 cm. tall when grown in pots, and approximately 20-25 cm. in diameter when fully grown.

*Leaves.*—General form: Broadly oval. Diameter: 5-6 cm. Texture: Soft hairy. Aspect: Velvet. Veins: Pronounced. Color (upperside): H.C.C. II ivy green 0001060/2. Color (underside): Purplish green. Petiole: Purplish green.

*Flowers.*—Buds: Ball-shaped; 7-10 or more per stem, and more with second flowering. Sepals: Color: Brownish green. Calyx: Flat funnel shape. Aspect: Hairy. Peduncle: Brownish green, slightly hairy.

*Individual flowers.*—Size: 3.0-3.5 cm. by 3.5-4 cm. in its longer direction. Color: Upperside: R.H.S. 77A. Underside: H.C.C. II pansy violet 033/1. Center: Royal purple 834. Borne: Upright, profuse and compact flowerhead. Shape: Single, violet shape. Flowering Time: A marketable plant is ready 8-10 weeks after potting.

*Reproductive organs.*—Stamens: 2, compound of 4 cells. Styles: Same purple color as flower. Pollen color: Dresden yellow 64.

*Roots.*—White when young and active; turning brownish when older.

*Disease resistance.*—Good as experienced to date.

General observations: South Dakota is principally characterized by the entirely unique violet purple flower color with intensive darker centers. This darkening at the center has not occurred in commercial African violet cultivars to date. The plant is very attractive, with the profuse type bouquet being positioned well above the foliage. The flowers are long lasting and non-dropping. The flowers fade somewhat on maturation.

I claim:

1. A new cultivar of African violet named South Dakota, as described and illustrated, and particularly characterized by its vigorous growth habit, profuse bouquet positioned on upright flower stems; deep violet purple flower color, with the centers of the flower being relatively darker; single flower form; dark green leaves, and its long lasting and non-dropping flowers.

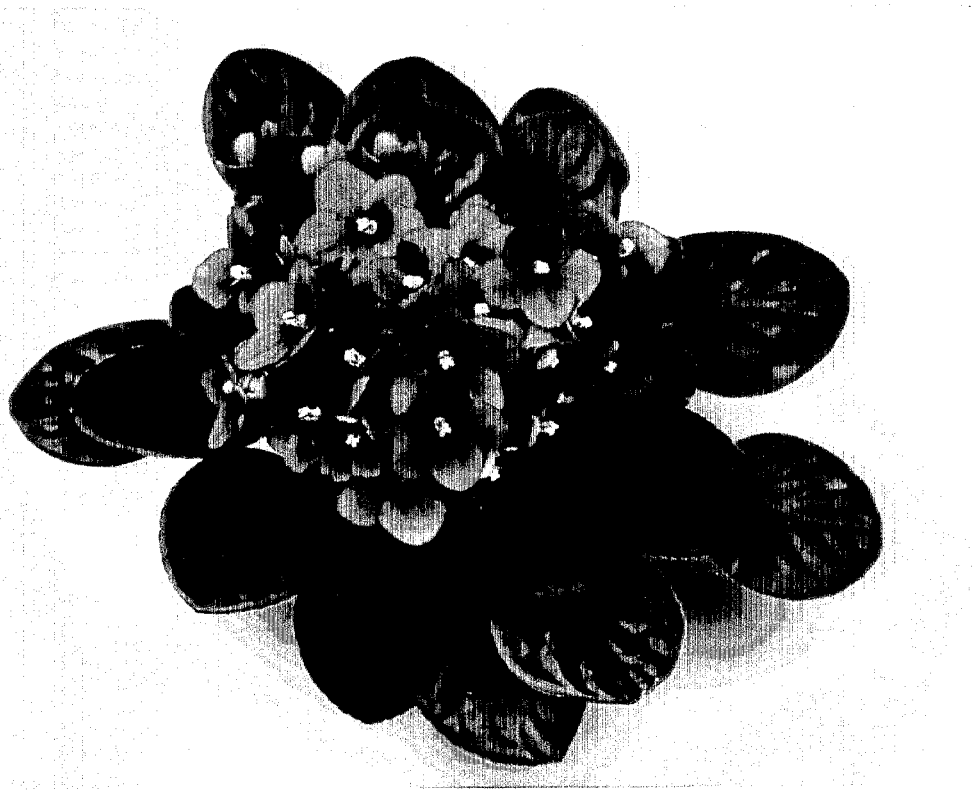

* * * * *